(12) United States Patent
Itai et al.

(10) Patent No.: US 6,490,588 B2
(45) Date of Patent: Dec. 3, 2002

(54) METHOD OF SEARCHING NOVEL LIGAND COMPOUNDS FROM THREE-DIMENSIONAL STRUCTURE DATABASE

(76) Inventors: Akiko Itai, 16-6, Hongo 5-chome, Bunkyo-ku, Tokyo (JP), 113; Miho Mizutani, Room 203, Mansion Kaneki, Koishikawa 5-chome, Bunkyo-ku, Tokyo (JP), 112

( * ) Notice: Subject to any disclaimer, the term of this patent is extended or adjusted under 35 U.S.C. 154(b) by 0 days.

(21) Appl. No.: 10/022,275

(22) Filed: Dec. 20, 2001

(65) Prior Publication Data

US 2002/0111938 A1 Aug. 15, 2002

Related U.S. Application Data

(63) Continuation of application No. 08/817,646, filed as application No. PCT/JP95/02219 on Oct. 30, 1995.

(30) Foreign Application Priority Data

Oct. 31, 1994 (JP) .............................................. 6-267688

(51) Int. Cl.[7] .............................................. G06F 17/30
(52) U.S. Cl. ....................................................... 707/10
(58) Field of Search ................................. 707/1–6, 104; 702/19, 22, 27; 703/11

(56) References Cited

U.S. PATENT DOCUMENTS

| | | | |
|---|---|---|---|
| 5,331,573 A | 7/1994 | Balaji et al. | 395/500.32 |
| 5,526,281 A | 6/1996 | Chapman et al. | 702/22 |
| 5,642,292 A | 6/1997 | Itai et al. | 702/27 |

FOREIGN PATENT DOCUMENTS

| | | |
|---|---|---|
| EP | 0633534 | 1/1995 |
| JP | 6309385 | 11/1994 |
| JP | 7133233 | 5/1995 |
| WO | 9320525 | 10/1993 |
| WO | 97/18180 | 5/1997 |
| WO | 97/24301 | 7/1997 |

OTHER PUBLICATIONS

Desjarlais et al., *Proc. Natl. Acad. Sci.*, USA, vol. 87, pp. 6644–6648, 1990.

(List continued on next page.)

*Primary Examiner*—Jack Choules
(74) *Attorney, Agent, or Firm*—Greenblum & Bernstein, P.L.C.

(57) ABSTRACT

A method of searching one or more ligand-candidate compounds to a target biopolymer from a three-dimensional structure database, which comprises the steps of: (i) the first step of assigning hydrogen-bonding category numbers, information for calculating force-field energy, and information for generating conformations to two or more trial compounds in addition to atomic three-dimensional coordinates thereof; (ii) the second step of preparing physicochemical information about a ligand-binding region and one or more dummy atoms based on the three-dimensional atomic coordinates of the target biopolymer; (iii) the third step of estimating the most stable docking structure, wherein said step further comprises the steps of examining possible docking structures by docking a trial compound to the biopolymer while varying conformations of the trial compound, evaluating interaction energies between the target biopolymer and the trial compound, and repeating structure optimization; (iv) the fourth step of deciding whether or not the trial compound should be adopted as a ligand-candidate compound based on given criteria including the interaction energy values between the target biopolymer and the trial compound in the most stable docking structure estimated according to the step (iii); and (v) the fifth step of repeating the step (iii) and the step (iv) for all of the trial compounds.

5 Claims, 4 Drawing Sheets

OTHER PUBLICATIONS

Moon et al., *Tetrahedron Computer Methodology*, vol. 3, No. 6C, pp. 697–711, 1990.

Itai et al., Structural Analysis of Malarial DHFR and Inhibitor Design, Report in Fiscal Year Heisei 6 (Mar. 1995) on "Chemistry of Natural Super Molecules" in the intensive field research made by a subsidy of the Ministry of Education, Mar. 1995, pp. 212–215.

Boehm, *Journal of Computer–Aided Molecular Design*, 6 (1992) 593–606.

Pearlman et al., *J. Of Comp. Chem.*, vol. 14, No. 10, pp. 1184–1193, 1993.

Gehlhaar et al., *J. Med. Chem.*, vol. 38, pp. 466–472, 1995.

Boehm, *Journal of Computer–Aided Molecular Design*, 6(1992)61–78.

Gillet et al, Journal of Computer–Aided Molecular Design, 7(1993)127–153.

Eisen et al., *Proteins: Structure, Function, and Genetics*, 19:199–221 (1994).

Inoue et al., "The 19th Symposium for Structure–Activity Relationship", subject No. 29S23, 1991, including pp. 316–319 and pp. 372 with English abstract.

Kanazawa et al. "The 20th Symposium for Structure–Activity Relationship", subject No. 27S22, 1992, including pp. 258–261 and pp. 322 with English abstract.

Takeda et al: "The 21st Symposium for Structure–Activity Relationship", subject No. 26S25, 1993, including pp. 321–324 including English abstract on pp. 324.

Ullman. *J. Assoc. Comput. Mach.*, vol. 23, pp. 31, 1976.

Sadowski et al. *Chem. Rev.*, vol. 93, pp. 2567–2581, 1993.

Tomoika et al. *J. Comput Aided Mol. Design*, vol. 8, pp. 347, 1994.

Kato et al. *Tetrahedron Lett.*, vol. 43, pp. 5229–5236, 1987.

Itai et al. "Molecular Symposium for Rational Drug Design" in 3DQSAR in Drug Design Theory, Methods and Applications, Ed. Kubinyi, H. ESCOM, Netherland, pp. 200–225, 1993.

Mizutani et al. *J. Mol. Biol.*, vol. 243, pp. 310–326, 1994.

Bolin, *J. Biol. Chem.*, vol. 257, pp. 13650, 1982.

Nishibata et al., *Tetrahedron*, vol. 47, pp. 8985–8990 (1991).

Nishibata et al., *J. Med. Chem.*, vol. 36, pp. 2921–2928 (1993).

Yamada et al., *J. Mol. Biol.*, vol. 243, pp. 310–326 (1994).

Mizutani et al., 24th Symposium for Structure Activity Relationship, Subject No. 14S20 (1996).

Gallop et al., *J. Med. Chem.*, vol. 37, pp. 1233–1251 (1994).

Burgess et al., *J. Med. Chem.*, vol. 37, 2985–2987 (1994).

Sadowski et al., *J. Chem. Rev.*, vol. 93, pp. 2567–2581 (1993).

Desjarlais et al., *J. Med. Chem.*, 31 (1988) pp. 722–729.

Fletcher and Powell, *Computer J.*, 6 (1968) p. 163–168.

Kabsch, *Acta Cryst.*, A32 (1976) p.922–923.

Warshel, *J. Phys. Chem.*, 83 (1979) pp. 1640–1652.

Kabsch, *Acta Cryst.*, A34 (1978) pp. 827–828.

Lam et al., *Science*, vol. 263 (1994) pp. 380–384.

Miller et al., *Journal of Computer–Aided Molecular Design*, 8 (1994) pp. 153–174.

Mizutani et al., *J. Mol. Biol.* 243 (1994) pp. 310–326.

Tomioka et al., *Journal of Computer–Aided Molecular Design*, 1 (1987) pp. 197–210

Weiner et al., *J. Am. Chem. Soc.*, 106 (1984) pp. 765–784.

Yamada and Itai, *Chem. Pharm. Bull.*, 41(6) (1993) pp. 1200–1202.

Yamada and Itai, *Chem. Pharm. Bull.*, 41(6) (1993) pp. 1203–1205.

Martin, Yvonne C., Computer Design of Potentially Bioactive Molecules by Geometric Searching with Aladdin, Tetrahedron Comp. Neuro. (1998) pp. 360–325.

Moon, J., and Howe, W., Proteins:, Struct., Funct., Genet. 11(4), pp.314–328 (1991).

Boehm, Hans J., Database accenssion No. 119:66291 CA XP002196006.

Boehm, Hans J., J. Computer–Aided Mol. Des. 6, pp. 61–78 (1992).

METHOD OF SEARCHING NOVEL LIGAND COMPOUNDS FROM THREE-DIMENSIONAL STRUCTURE DATABASE

This application is a continuation of U.S. application Ser. No. 08/817,646, filed Jun. 5, 1997, which is hereby incorporated by reference in its entirety, and which is a National Stage application of PCT/JP95/02219, filed Oct. 30, 1995, which was not published in English under PCT Article 21(2). The present application claims priority under 35 U.S.C. §§119 of Japanese Application Nos. 6-267688 filed Oct. 31, 1994.

TECHNICAL FIELD

The present invention relates to a method of searching a three-dimensional structure databases, which can be utilized for finding novel lead-structures of medicaments, pesticides, and other biologically active compounds.

BACKGROUND ART

Medicaments generally exhibit their biological activities through strong interactions with target biopolymers. In recent years, three-dimensional structures of biopolymers, which play important roles in living bodies, have been revealed successively on the basis of progresses in X-ray crystallographic analyses and NMR technology. With the advance of these researches, methodologies of theoretical approach based on information about three-dimensional structures of biopolymers and their successful results have been reported with respect to lead generations of new drugs, which were conventionally achieved mostly by random screenings or accidental discoveries. Importance of such approach is recognized with increasing interest, and researches from various viewpoints have been conducted in all the world.

An object of these researches is to provide a process for creation of ligand candidate structures by means of a computer. Another object is to provide a process for searching for ligand structures from a three-dimensional structure database containing known compounds. The former (automatic structure construction approach) is advantageous in that the process can suggest a wide variety of possible ligand structures irrespective of known or unknown structures. On the other hand, the latter (database approach) is used in searching for novel biologically active compounds from databases comprised of accumulated structures of known compounds. When a search is applied to a database which consists of compounds stocked in an own company or commercially available compounds, this method is particularly advantageous in that compounds, this method is particularly advantageous in that compounds found to reach criteria of hit ("hit compounds") can be obtained without any synthetic efforts, and their association constants to target biopolymers and biological activities can be measured.

Synthesis of a compound with a novel molecular skeleton generally needs several months even for an expert, and accordingly, years of and burden of work are required to synthesize a lot of promising structures and measuring their activities. However, if hit compounds are already available, measurements of association constants and biological activities can be easily performed for dozens of promising ligand candidate compounds. In addition, based on the structure of a compound found to have a considerable extent of high association constant or activity, an efficient lead generation is achievable by designing compounds with higher association constants and biological activities and synthesizing the compounds. For these reasons, approaches have recently been interested which comprises the steps of searching three-dimensional structure databases consisting of known compounds and discovering novel pharmacologically active compounds.

However, one of problems of this method is by what query the search is carried out. Generally, a three-dimensional structure database is searched by queries of whether or not given atomic groups or functional groups exist which are presumed as essential for the desired activity in typical biologically active compounds used as templates, or alternatively, whether or not their relative positions are similar to those of the template compounds. Where the structure of a target biopolymer is unknown, basically no approach can be relied on other than this process. However, since these queries are based on assumptions and hypotheses, hit compounds may often fail to have the same activity as that of the template compounds. Where two or more molecules with quite different structural features exhibit similar activities, it can only become possible to create more probable operating hypotheses, with reference to functional groups essential for the activity and their relative positions, by means of structural information about these molecules.

The most difficult problem in the search of three-dimensional structure databases lies in the handling of conformational flexibility of compounds. It has been known that the conformations of a ligand as it binds to a biopolymer (i.e., the most stable complex is formed) do not necessarily accord with any of stable structures of the molecule itself, in the state of a crystal or a solution, or a structure with the most stable energy obtained by energy calculation, and that one ligand molecule can form stable complexes in different conformations depending on target biopolymers. Generally, a set of atomic coordinates representing a three-dimensional structure of one conformation among multiple possible conformations is contained as for one compound in a database. Furthermore, except for databases derived from crystal structures, information of three-dimensional structure of each compound is obtained from two-dimensionally inputted structure through calculation. These three-dimensional structures often represent one of local minimum structures that can be taken by the molecule, per se.

Therefore, if a search is carried out merely on the basis of conformations contained in a database to judge whether or not compounds meet the criteria of hit, most compounds fail to be selected which should be hit if other conformations are considered. Although the number of conformations to be considered may vary depending on the number of rotatable bonds, as well as factors such as degrees of precise consideration of conformations, several tens to hundreds of thousands conformations should be taken into account for a moderately flexible molecule containing 3 to 6 rotatable bonds. In order to consider these possible conformations, available processes are limited to either of those comprising the steps of selecting promising conformations and inputting them in a database beforehand, or alternatively, generating conformations and examining at the time of conducting a search. In any events, enormous computer resources and calculation time are required.

Recently, Kearsley et al. with Merck prepared a database which comprises 20 conformations at most for a single compound and reported "FLOG," a searching system in which a search is carried out using searching standard mainly consisting of relative positions of functional groups (M. D. Miller, S. K. Kearsley, D. J. Underwood, and R. P. Sheridan: Journal of Computer-Aided Molecular Design, 8, 1994, pp.153–174, FLOG: A system to select 'quasi-flexible' ligands complementary to a receptor of known three-dimensional structure). It was reported that the FLOG took approximately one week to complete searching a database containing 2,000,000 conformations for 100,000 compounds by means of a super computer CRAY. The twenty conformations in average for each compound are stored by selecting energetically stable local minimum structures through prior conformational analysis of each compound, for which enormous time and burden of work are needed. Nevertheless, twenty conformations per a single compound are insufficient.

In addition, the method adopts the query which comprise the presence or absence of functional groups presumably essential for the activity of a compound as a template, as well as distance, angle, or direction between the groups. These queries are most plain among possible queries, and although they have advantages to shorten calculation time using simple algorithm, high probability cannot be expected that hit compounds actually have the desired activity. The reason lies in that a molecule having inappropriate whole molecular shape and size fails to exhibit activity, even if functional groups merely have desired relative positions. If a three-dimensional structure of the target biopolymer is known, the most effective search can be achieved by means of such information, which provides high probability that hit compounds have the desired activity.

For example, Eyermann et al. with Dupont Merck performed a database search based on relative positions of functional groups of ligand molecules which had been analyzed by X-ray crystallography as a complex with a biopolymer (P. Y. S. Lam, P. K. Jadhav, C. J. Eyemann, C. N. Hodge, Y. Ru, L. T. Bacheler, J. L. Meek, M. J. Otto, M. M. Rayner, Y. N. Wong, C. H. Chang, P. C. Weber, D. A. Jackson, T. R. Sharp, and S. Erickson-Viitanen: Science, 263, 1994, pp.380–384, Rational design of Potent, Bioavailable, Nonpeptide Cyclic Ureas as HIV Protease Inhibitors.). In the HIV protease system, compounds were searched for as to criteria where the three positions of an oxygen atoms in water molecules are in similar relative positions which connect the protease to the ligand through hydrogen bonds at the centers of two benzene rings in the peptide ligand molecule. Among the hit compounds, one compound was selected which well fitted into the ligand-binding region and formed hydrogen bonds other than those formed by the oxygen atoms used as query. They reported that a compound with high activity was developed based on the structure of this compound by repeated works of synthesizing compounds with appropriate modifications while measuring inhibitory activities against the enzyme. However, the publication lacks detailed descriptions as for the search process, and their technique of handling conformations is not deducible.

The search query capable of providing the highest probability that hit compounds have desired activity is that whether or not compounds stably bind to a ligand-binding region of the target biopolymer. Although in some cases the desired activity fails to be exhibited due to physicochemical factors such as water solubility even if a compound satisfies the criteria, reaching the criteria is an essential requirement for the expression of activity. On the other hand, the presence or absence of specific functional groups and the relative positions of functional groups are not necessarily essential for the expression of activity, and even if a compound falls within a different family and has dissimilar skeletal structure to the known active structures, the compound may possibly exhibit the same activity if it can form a complex between the target biopolymer at a similar extent of stability. Therefore, compounds satisfying the criteria that they can stably bind to a ligand-binding region of the target biopolymer have high probability of being actual candidates as ligands. In other words, by using the criteria of fitting to a ligand-binding region of the target biopolymer, it becomes possible to identify compounds which exhibit the desired biological activity and have a wide variety of structures from databases.

In order to determine whether or not a given ligand molecule can bind to the target biopolymer, it is necessary to find the most stable docking structure among possible docking structures and to know the degree of stability of the docking structure. Also, in order to find the most stable docking structure between a given biopolymer and a ligand molecule, it is necessary to estimate stabilities of all docking structures by considering all possible binding modes (corresponding to rotation or translation of one molecule while fixing another compound), and possible ligand conformations. However, since the process needs enormous calculation, it cannot be achieved by interactive methods using a graphic display. Therefore, the development of an automatic docking method has been desired which can perform the above process automatically and efficiently.

As automatic docking methods, Kuntz et al. developed a method for estimating possible binding modes by representing the shape of a ligand-binding region by means of several to dozens of inscribed spheres and comparing a set of vectors formed by the centers of the spheres with a set of intramolecular vectors of a ligand compound (R. L. Desjarlais, R. P. Sheridan, G. L. Seibel, J. S. Dixon, I. D. Kuntz and R. Venkataraghavan: J. Med. Chem. 31 (1989) 722–729). Using Shape Complementarity as an Initial Screen in Designing Ligands for a Receptor-Binding Site of Known 3-Dimensional Structure.). In a recent improved process, the process is modified so that intermolecular energy can be calculated in addition to the score representing coincidence between the vectors.

However, this method is disadvantageous because it needs an undue time even only for covering all binding modes. Some improved processes include alternations so that conformations can be varied for the docking of a single compound. However, the processes are not designed so as to provide an automatic procedure covering all of the docking processes. Although energy evaluation can be done concerning hit compounds, only simple scores can be calculated and hydrogen bonds or the like are disregarded during the docking process. Furthermore, its accuracy is insufficient, i.e., there is a problem in that, for example, the true docking structure determined by crystal analysis fails to be judged as the highest rank and is sometimes judged as rather low in rank. Moreover, its unavoidable defect is in that the process is carried out fundamentally by a fixed conformation for each compound, and conformational flexibilities cannot be handled. In a manual operation cannot compensate for the above defect especially, its practical utility is low in a three-dimensional database search which requires full automatic operation for numerous compounds.

The inventors of the present invention developed "ADAM," a method for estimating the most stable docking structures of a biopolymer and a ligand molecule automatically and without any preconception, and they successfully solved all of the aforementioned problems (PCT/JP93/0365, PCT International Publication WO 93/20525; M. Yamada and A. Itai, Chem. Pharm. Bull., 41, p. 1200, 1993; M. Yamada and A. Itai, Chem. Pharm. Bull., 41, p. 1203, 1993; and M. Yamada Mizutaui, N. Tomioka and A. Itai, J. Mol. Biol., 243, pp. 310–326, 1994).

In the applications of "ADAM" to several enzyme-inhibitor systems whose structures had been elucidated by crystallographic analyses, all the resulted docking models with minimum energy perfectly reproduced the structure in the crystal, and torsion angles of rotatable bonds in the ligand molecule and hydrogen-bonding schemes were also accurately reproduced. The high accuracy of "ADAM" is based on the calculations of structure optimization (energy minimization) performed altogether three times. Though the time required may vary depending on the performance of a computer, numbers of dummy atoms, number of heteroatoms, number of rotatable bonds and the like and cannot be generalized, it takes from several minutes through approximately 1 hour to obtain an initial docking model with an ordinary drug molecule by means of a commonly used workstation (R4400). This speed is dozens of times faster than the fastest method which handles possible conformations reported so far.

However, although ADAM is suitable in searching for the most stable docking structure between the target biopolymer and a single ligand molecule, the method is not suitable for searching novel ligand compounds from a wide variety of numerous compounds contained in a three-dimensional structure database as it is. Therefore, further improvement has been desired.

Accordingly, an object of the present invention is to provide a method suitable for searching novel ligand compounds from a wide variety of numerous compounds, thereby solving the problems of the state of the art.

SUMMARY OF THE INVENTION

The inventors of the present invention performed various researches. As a result, they succeeded in developing a process for selecting one or more promising ligand candidates from an enormous number of trial compounds: wherein the process comprises the steps of estimating the most stable docking structure for each trial compound; and selecting one or more ligand candidate compounds from all the trial compounds by given criteria including the interaction energy between the target biopolymer and the trial compound in the most stable docking structures; and the aforementioned step of estimating the most stable docking structure for each trial compound comprises the steps of: evaluating all possible docking structures generated through docking of the trial compound to the biopolymer, while varying conformation of the trial compound and repeating structural optimizations, based on interaction energies between the biopolymer and the trial compound, e.g., hydrogen bonds, electrostatic interaction, and van der Waals force. The present invention was achieved on the basis of these findings.

The present invention thus provides a method of searching one or more ligand compound to a target biopolymer from a three-dimensional structure database, which comprises the steps of:

(i) the first step of assigning hydrogen-bonding category numbers, information for calculating force-field energies, and information for generating conformations, to two or more trial compounds, in addition to three-dimensional atomic coordinates thereof;

(ii) the second step of preparing physicochemical information about a ligand-binding region and one or more dummy atoms based on the three-dimensional atomic coordinates of the target biopolymer;

(iii) the third step of estimating the most stable docking structure, wherein said step further comprises the steps of generating possible docking structures by docking a trial compound to the biopolymer while varying conformations of the trial compound, and evaluating interaction energy between the target biopolymer and the trial compound, based on the hydrogen-bonding category number, the information for calculating force-field energies, and the information for generating conformations assigned to the trial compound in addition to the three-dimensional atomic coordinates according to the step (i) and based on the physicochemical information about the ligand-binding region prepared in the step (ii):and then;

(iv) the fourth step of deciding whether or not the trial compound should be adopted as a ligand-candidate compound based on given criteria including the interaction energy values between the target biopolymer and the trial compound in the most stable docking structure found according to the step (iii); and (v) the fifth step of repeating the step (iii) and the step (iv) for all of the trial compounds.

The method of the present invention may comprise the sixth step of further selecting the ligand-candidate compounds selected in the step (iv) based on different criteria including the number of hydrogen bonds formed between the target biopolymer and/or interaction energy values derived therefrom.

DETAILED DESCRIPTION OF THE INVENTION

In the method of the present invention, the trial compounds are not particularly limited so long as their structures are known. For example, various compounds contained in currently available databases can be used. The hydrogen-bonding category numbers are identification numbers for functional groups capable of forming hydrogen bonds, and assigned to heteroatoms that directly participate in hydrogen bonds by the functional groups. By referring to the number, a geometric structure of the functional group and the nature of the hydrogen bond as well as the position of partner hydrogen-bonding atoms (dummy atoms) are instantly generated. The information for calculating force field energies includes an atom type number to discriminate atomic element and the state of hybridization of each atom that are used for calculating intramolecular and intermolecular interaction energies by means of molecular force field. The information includes an atomic charge assigned to each atom. The information for preparing conformations is used for systematically generating different conformations by varying torsion angles of rotatable bonds, in the range of the given initial and final values of the torsion angles by given values of step angle. It includes, for one bond to be rotated, a set of four atomic numbers constituting the torsion angle, and the initial and final values of the torsion angle and a step angle of rotation.

The term "biopolymer" means biological macromolecules and includes artificial mimetic molecules based on biological macromolecules. The term "physicochemical information about the ligand-binding region" means potential influence brought by all of the atoms of the biopolymer inside a cavity space of the biopolymer to which a ligand can bind. The meaning includes hydrogen-bonding properties of three-dimensional grid points within the ligand-binding region (hydrogen bond acceptor or hydrogen bond donor), and van der Waals interaction energies and electrostatic interaction energies generated between the biopolymer and probe atoms when the probe atoms are placed on the three-dimensional grid points. The meaning of "docking" is used to include the step of forming a complex from a trial compound molecule and a biopolymer, including the step of finding a stable docking structure formed by the both of them. The docking can generally be performed by interactive methods using computer graphics, as well as by automatic docking methods as the case may be.

The term "interaction between a biopolymer and a trial compound" is a force arisen between the biopolymer and the trial compound, whose examples include hydrogen bond, electrostatic interaction, van der Waals interaction and the like. The term "ligand" or "ligand compound" is a compound with low molecular weight that binds to a biopolymer, whose examples include medicaments, substrates and inhibitors of enzymes, coenzymes, and other biologically-active substances.

According to an embodiment of the method of the present invention, the above third step may comprise the following steps:

(1) step (a) of searching likely binding modes between the biopolymer and the trial compound by preparing all of the combinatorial correspondences between hydrogen-bonding heteroatoms in the trial compound and dummy atoms placed at the positions of heteroatoms that can be hydrogen-bonding partners of hydrogen-bonding functional groups in the biopolymer;

(2) step (b) of simultaneously estimating possible hydrogen-bonding schemes between the biopolymer and the trial compound and conformations of hydrogen-bonding part of the trial compound by comparing the distances between dummy atoms with the distances between the corresponded hydrogen-bonding heteroatoms while systematically changing the conformations of the trial compound; and (3) step (c) of obtaining the structure of a docking structure comprising the biopolymer and the trial compound by converting the atomic coordinates of the trial compound to the coordinate system of the biopolymer for each hydrogen-bonding scheme and conformation obtained in the step (b) based on the correspondences between the hydrogen-bonding heteroatoms in the trial compound and the dummy atoms.

In addition, according to another embodiment of the method of the present invention, the above third step may comprise the following steps:

(1) step (a) of searching likely binding modes between the biopolymer and the trial compound by preparing all of the combinatorial correspondences between hydrogen-bonding heteroatoms in a partial structure of the trial compound and the dummy atoms placed at the positions of heteroatoms that can be hydrogen-bonding partners of hydrogen-bonding functional groups in the biopolymer;

(2) step (b) of simultaneously estimating hydrogen-bonding schemes between the biopolymer and the trial compound and conformations of the partial structure of the trial compound by comparing the distances between dummy atoms with the distances between the corresponded hydrogen-bonding heteroatoms while systematically changing the conformations of the trial compound;

(3) step (c) of preserving correspondences of the dummy atoms and the hydrogen-bonding heteroatoms that provide impossible hydrogen-bonding schemes in the partial structure of the trial compound, and hydrogen-bonding heteroatoms that cannot form any hydrogen-bond with the dummy atoms based on the hydrogen-bonding schemes and conformations obtained in the step (b);

(4) step (d) of searching likely binding modes between the biopolymer and the trial compound by preparing all of the combinatorial correspondences between dummy atoms and hydrogen-bonding heteroatoms in a the whole structure of the trial compound, excluding the correspondences containing the hydrogen-bonding heteroatoms preserved in the step (c) and the correspondences containing the dummy atoms and hydrogen-bonding heteroatoms preserved in the step (c);

(5) step (e) of simultaneously estimating possible hydrogen-bonding schemes between the biopolymer and the trial compound and conformations of hydrogen-bonding part of the trial compound by comparing the distances between dummy atoms with the distances between corresponded hydrogen-bonding heteroatoms while systematically changing the conformations of the trial compound; and (6) step (f) of obtaining the structure of a docking structure comprising the biopolymer and the trial compound by converting the atomic coordinates of the trial compound to the coordinate system of the biopolymer for each hydrogen-bonding scheme and conformations obtained in the step (e) based on the correspondences between the hydrogen-bonding heteroatoms in the trial compound and the dummy atoms.

When the third step includes the above sub-steps, it becomes possible to accelerate the search for stable docking structures consisting of the biopolymer and the trial compound, and in addition, it also become possible to search for stable docking structures including the most stable docking structure in short time even where the biopolymer and/or the trial compounds have complicated structures.

According to a further embodiment of the method of the present invention, the above third step may comprise the following steps:

(1) step (a) of searching likely binding modes between the biopolymer and the trial compound by preparing all of the combinatorial correspondences between hydrogen-bonding heteroatoms in the trial compound and dummy atoms placed at the positions of heteroatoms that can be hydrogen-bonding partners of hydrogen-bonding functional groups in the biopolymer;

(2) step (b) of simultaneously estimating possible hydrogen-bonding schemes between the biopolymer and the trial compound and conformations of hydrogen-bonding part of the trial compound by comparing the distances between dummy atoms with the distances between hydrogen-bonding heteroatoms while systematically changing the conformations of the trial compound;

(3) step (c) of optimizing the conformations of the trial compound so that the positions of the dummy atoms and the hydrogen-bonding heteroatoms in the trial compound can be in accord with each other while retaining the hydrogen-bonding scheme obtained in the step (b), and then excluding the conformations of the trial compound having high intramolecular energies;

(4) step (d) of obtaining the structure of a complex comprising the biopolymer and the trial compound by converting the entire atomic coordinates of the trial compound to the coordinate system of the biopolymer for each conformation not excluded in the step (c) based on the corresponding relationships between the hydrogen-bonding heteroatoms in the trial compound and the dummy atoms;

(5) step (e) of excluding from docking structures of hydrogen-bonding parts obtained in the step (d) the docking structures in which intramolecular energies of the hydrogen-bonding parts of the trial compound and intermolecular energies between the biopolymer and the hydrogen-bonding parts of the trial compound are high, and then carrying out structure optimizations of the remaining docking structures;

(6) step (f) of obtaining new docking structures comprising the whole trial compound by generating the conformations of non-hydrogen-bonding parts of the trial compound for each docking structure obtained in the step (e); and (7) step (g) of excluding from the docking structures obtained in the step (f) the docking structures in which intramolecular energies of the whole structure of the trial compound and intermolecular energies between the biopolymer and the trial compound are high, and then carrying out structure optimizations of the remaining docking structures.

When the third step includes the aforementioned substeps, it becomes possible to select appropriate docking structures even when reduced numbers of conformations are initially generated, and thereby obtain stable docking structures with high accuracy.

In the above methods, the hydrogen-bonding functional groups include functional groups or atoms that can participate in the formations of hydrogen bonds. The term "hydrogen-bonding heteroatoms" means heteroatoms which exist in the hydrogen-bonding functional groups present in the trial compounds. The term "hydrogen-bonding part" means a partial structure of the trial compound structure which comprises all the hydrogen-bonding heteroatoms that are corresponded to dummy atoms, and the term "non-hydrogen-bonding part" means a partial structure other than the hydrogen-bonding part.

According to a still further embodiment of the present invention, there is provided a method for preparing a three-dimensional structure database which comprises the step of optionally adding three-dimensional coordinates of hydrogen atoms, and adding atom type numbers, hydrogen-bonding category numbers, atomic charge, and modes of bond rotation in addition to three-dimensional coordinates of trial compounds.

Figure 1:
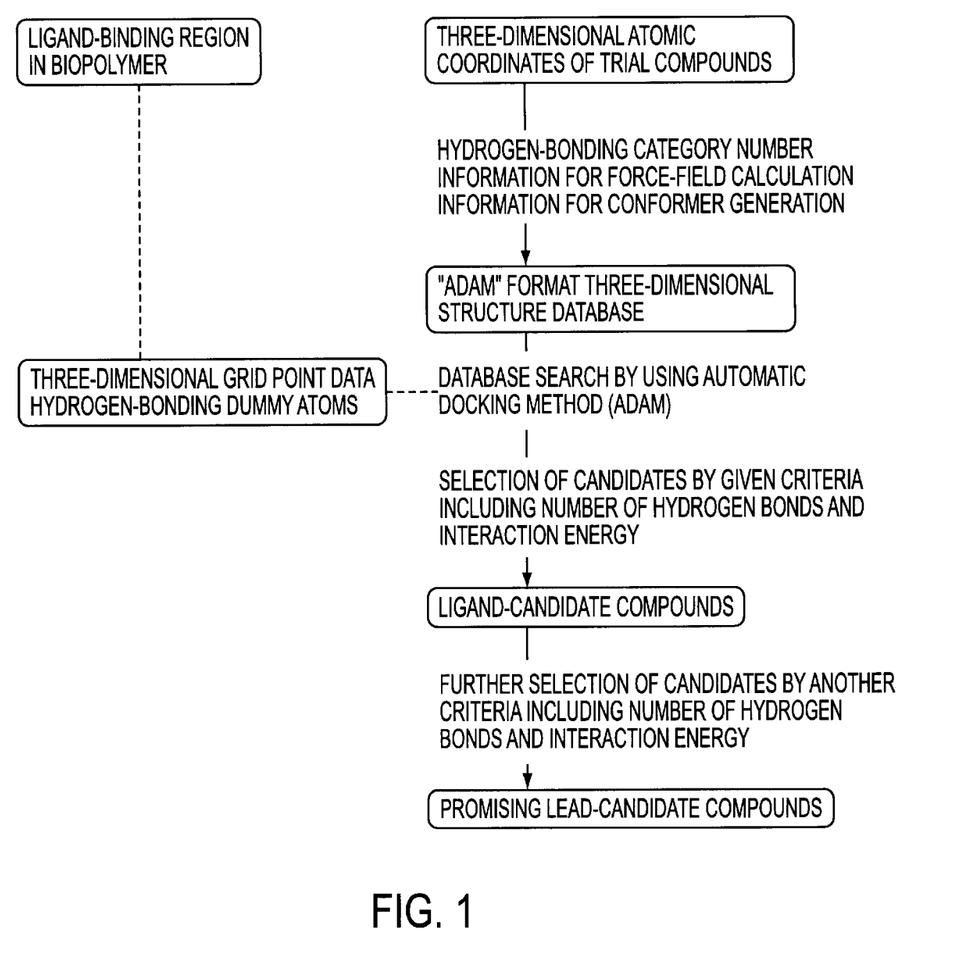
FIG. 1 shows a conceptual scheme by featuring the method of the present invention.
Figure 2:
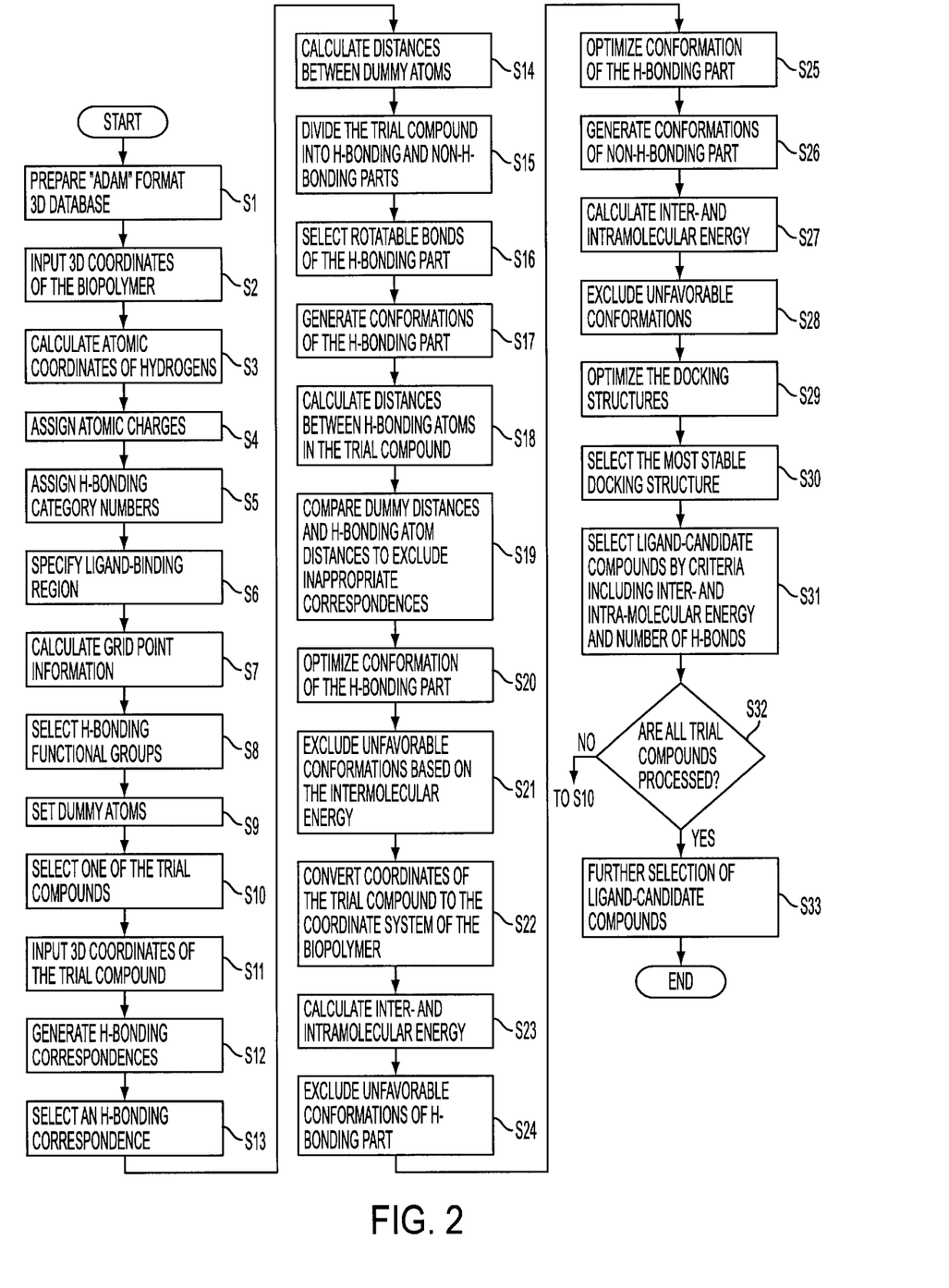
FIG. 2 is a flowchart according to an embodiment of the method of the present invention. In the figure, S represents each step.

Preferred embodiments of the present invention will be explained below by referring to the flowchart shown in FIG. 2. In FIG. 2, the symbol "S" represents each step and the name "ADAM" represents the method for searching a stable docking structure of biopolymer and ligand molecules disclosed in International Publication WO93/20525 (International Publication Date: Oct. 14, 1993). The disclosure of the specification and claims of the International Publication WO93/20525 is herein incorporated by reference.

The "ADAM" format three-dimensional database is first prepared which comprises at least two trial compounds. The aforementioned database can be prepared, for example, by the method explained below. Three-dimensional coordinates of trial compounds are first inputted. As the three-dimensional coordinates of the trial compounds, coordinates obtained by converting two-dimensional coordinates obtainable from a two-dimensional database to a three-dimensional coordinates through force-field calculation, or coordinates obtained from structural analysis of a single crystal as well as those from crystal database, or those from three-dimensional structures obtained by model building procedure based on energy calculation may be used. As regards three-dimensional structures of each trial compound, conformations are basically not necessary to be taken into account so long as geometric values such as bond distances and bond angles between the atoms are accurate. However, in order to calculate atomic charge of each atom in the trial compound as accurately as possible, it is preferred to input atomic coordinates of a relatively stable structure.

After inputting the above three-dimensional coordinates of the trial compounds, a three-dimensional database can be prepared automatically by adding hydrogen atoms if necessary, and assigning a force-field atom-type number to each atom, hydrogen-bonding category numbers to hydrogen-bonding heteroatoms, atomic charge to each atom, and modes of bond rotations (for example, information about covalent bonds to be rotated, values of initial, final, and increment torsion angles of the rotation).

The force-field atom-type numbers for each atom in the trial compound can be assigned, for example, according to the numbering method of Weiner et al. (Weiner, S. J., Kollaman, P. A., Case, D. A., Singh, U. C., Ghio. C., Alagona, G., Profeta, S., Jr., and Weiner, P., J. Am. Chem. Soc., 106, 1984, pp. 765–784). The hydrogen-bonding catagory numbers for hydrogen-bonding heteroatoms in the trial compound can be assigned according to the following Table 1. The atomic charge of each atom in the trial compound can be calculated, for example, by the Gasteiger method or by molecular orbital calculation with MNDO, AM1 or other method in the MOPAC program. As for the mode of bond rotation, it is preferred to indicate to rotate all rotatable bonds systematically with rotation-angle intervals of 60° to 120°.

TABLE 1

A List of Hydrogen-Bonding Hereroatoms and their Hydrogen-Bonding Category Numbers included in Hydrogen-Bonding Functional Groups

| Hydrogen-Bonding Category Number | Heteroatoms included in Hydrogen-Bonding Functional Groups |
|---|---|
| 1 | $sp^2$ N in Primary Amines |
| 2 | $sp^3$ N in Primary Amines |
| 3 | $sp^3$ N in Ammonium Ions |
| 4 | $sp^2$ N in Amides |
| 5 | $sp^3$ N in Secondary Amines |
| 6 | N in Aromatic Groups |
| 7 | Protonated N in Aromatic Groups |
| 8 | N in Tertiary Amines |
| 9 | Protonated N in Tertiary Amines |
| 10 | O in Hydroxyls with Rotatable C-O bond |
| 11 | O in Ethers |
| 12 | O in Carbonyls |
| 13 | O in Carboxylate Anions |
| 14 | O in Carboxylic Acids |
| 15 | O in Phosphates |
| 16 | O in Water Molecules |
| 17 | S in Mercaptos |
| 18 | S in Thioethers |
| 19 | O in Hydroxyls with fixed hydrogen atom positions |

Then, the number of atoms in the biopolymer and their atomic coordinates (except for atomic coordinates of hydrogen atoms) are inputted (S2). As regards the atomic coordinates of the biopolymer, three-dimensional information obtained by X-ray crystallographic analyses or NMR analyses, information obtainable from the protein crystal structure database and the like, or alternatively, atomic coordinates of a biopolymer model constructed on the basis of such information or the like may be used. The atomic coordinates of the biopolymer are preferably provided as a three-dimensional coordinate system. In addition, cofactors that bind to the biopolymer and that structurally as well as functionally play important roles may be considered as a part of the biopolymer, and the atomic coordinates of the biopolymer in the state of being bound with the cofactor may be inputted to perform the successive steps. Examples of the cofactors include coenzymes, water molecules, metal ions and the like.

Following the above step, the atomic coordinates of the hydrogen atoms in amino acid residues present in the biopolymer are calculated (S3). In general, it is difficult to determine the positions of hydrogen atoms in biopolymers by experimental procedures such as X-ray crystallographic analyses or NMR analyses. In addition, the information about hydrogen atoms is not available from protein crystal structure databases or the like. Therefore, it is necessary to calculate the atomic coordinates of the hydrogen atoms in amino acid residues on the basis of the structures of the amino acid residues present in the biopolymer. For hydrogen atoms whose atomic coordinates cannot be uniquely determined as they bind to rotatable group of atoms in the amino acid residues, their atomic coordinates are preferably calculated on the assumption that they exist at trans positions.

Subsequently, atomic charges are appended to the atoms in amino acid residues present in the biopolymer (S4), and then hydrogen-bonding category numbers are assigned to the heteroatoms in hydrogen-bonding functional groups present in the biopolymer (S5). As the values of the atomic charges, reported values calculated for each amino acid, for example, values reported by Weiner et al. can be used (Weiner, S. J., Kollman, P. A., Case, D. A., Singh, U. C., Ghio, C., Alagona, G., Profeta, S., Jr. and Weiner, P., J. Am. Chem. Soc., 106, 1984, pp. 765–784). The hydrogen-bonding category numbers can be assigned according to the Table 1.

A ligand-binding region is then specified (S6). As the ligand-binding region, spaces containing any part of the biopolymer can be specified by using preferably a rectangular box. Depending on the purposes, a ligand-binding pocket and its surrounding region of the biopolymer can be specified. If desired, a region containing any site in the biopolymer which binds a different molecule such as an effector and the like can also be specified. The term "ligand-binding region" means a cavity on the concaved surface of the biopolymer to which a ligand molecule such as a substrate or an inhibitor bind. For assigning the range of the ligand-binding region, a part of the functions of the program "GREEN" can be used (Tomioka, N., Itai, A. and Iitaka, Y., Journal of Computer-Aided Molecular Design, vol. 1, 1987, pp. 197–210 ).

Three-dimensional grid points are generated inside the ligand-binding region specified in the step S6, and for each three-dimensional grid point, an address number is assigned and grid point information is calculated (S7). The term "three-dimensional grid points" means the points on the three-dimensional lattice generated at a certain regular intervals within the ligand-binding region in the biopolymer. The meaning of "grid point information" includes local physicochemical character at each grid point in the ligand-binding region such as van der Waals interaction energies and electrostatic interaction energies arisen between the biopolymer and probe atoms, as well as hydrogen-binding properties. Wherein the van der Waals and electrostatic interaction energies are calculated on the assumption that probe atoms exist on each three-dimensional grid point. By using the grid point information on the three-dimensional grid points, it becomes possible to accelerate approximate calculations of the intermolecular interactions between the biopolymer and the trial compound to be carried out in the successive steps. In addition, reasonable determination of the positions of the dummy atoms, which is provided in the following steps, becomes achievable. As a result, possible docking structures comprising the biopolymer and the trial compound can be entirely searched in a short time.

The three-dimensional grid points may be generated at intervals of 0.3–2.0 angstroms, preferably 0.3–0.5 angstroms in the region specified in the step S6. As the probe atoms, all sorts of atoms contained in possible ligand compounds are preferably included. The van der Waals interaction energy that acts between each atom placed on the three-dimensional grid points and the biopolymer can be calculated according to a conventional atom-pair type calculation using an empirical potential function. As the empirical potential function, the Lennard-Jones type function represented by the following equation can be used.

$$G_{vdw,i} = \sum_j (A/r_{ij}^{12} - B/r_{ij}^6)$$

In the formula, symbol "i" is a sequential number representing a probe atom; and symbol "j" is a sequential number for the biopolymer atoms. Symbols "A" and "B" are parameters for determining the location and the magnitude of minimum potential. Symbol "$r_{ij}$" is an inter-atomic distance between the i-th probe atom and the j-th atom in the biopolymer. As the parameters "A" and "B," the values reported by Weiner et al. can be used (Weiner, S. J. Kollman, P. A., Case, D. A., Singh, U. C., Ghio, C. Alagona, G., Profeta, S., Jr. and Weiner, P., J. Am. Chem. Soc., 106, 1984, pp. 765–784).

The van der Waals interaction energy between the trial compound and the biopolymer, when the trial compound is placed on the three-dimensional grid points, can be calculated by the following equation:

$$E_{vdw} = \sum_{m=1}^{N} G_{vdw,m_0}$$

wherein "m" is the sequential number for each atom in the trial compound; N is the total number of atoms in the trial compound; and "$m_0$" is the sequential number of the three-dimensional grid point that is closest to the m-th atom.

The electrostatic interaction energy that generates between each probe atom placed on each three-dimensional grid point and the biopolymer can be calculated by the following equation:

$$G_{elc,i} = \sum_j K q_j / \varepsilon r_{ij}$$

wherein symbols "i," "j," and "$r_{ij}$" are the same as those defined above; "$q_j$" is the atomic charge of the j-th atom in the biopolymer; "K" is a constant for converting an energy unit; and "∈" is a dielectric constant. As the dielectric constant, a fixed value may be used, or alternatively, it is preferably to use a value depending on $r_{ij}$, as proposed by Warshel et al. (Warshel, A., J. Phys. Chem., 83, 1979, pp. 1640–1652).

The electrostatic interaction energy between the trial compound and the biopolymer, when the trial compound is placed on the three-dimensional grid points, can be calculated by the following equation:

$$E_{elc} = \sum_{m=1}^{N} q_m G_{elc,m_0}$$

wherein m, N and $m_0$ are as defined above.

The term "hydrogen-bonding grid point information" means information indicating that either hydrogen-donor or hydrogen-acceptor atom can form a hydrogen bond with the hydrogen-bonding functional group in the biopolymer if it is placed on the three-dimensional grid point, or alternatively that both hydrogen-donor and hydrogen-acceptor atom can (or cannot) form a hydrogen bond with the hydrogen-bonding functional group in the biopolymer if it is placed on the three-dimensional grid point. For example, the hydrogen-bonding information of three-dimensional grid points can be expressed by assigning number 1 for a three-dimensional grid point as a hydrogen-bond acceptor, number 2 for a three-dimensional grid point as a hydrogen-bond donor, number 3 on a three-dimensional grid having both properties, and number 0 on a three-dimensional grid having no hydrogen-bonding property.

The hydrogen-bonding grid point information can be obtained as set forth below. If the distance "DP" between a three-dimensional grid point "P" and a hydrogen-donating atom "D" in the biopolymer is within a range (e.g., 2.5–3.1 Å) that allows for the formation of a hydrogen bond, and if the angle ∠DHP made by the three-dimensional grid point "P", hydrogen "H," and atom "D" is within a range (e.g., more than 30°) that allows for the formation of a hydrogen bond, the three-dimensional grid point is determined to have property of hydrogen-bond acceptor. Similarly, if the distance "PA" between three-dimensional grid point "P" and hydrogen-accepting atom "A" in the biopolymer is within a range that allows for the formation of a hydrogen bond and if the angle ∠ALP which is made by the three-dimensional grid point "P," a lone-pair electron "L," and the hydrogen-accepting atom "A" is within a range that allows for the formation of a hydrogen bond, the three-dimensional grid point is determined to have the property of hydrogen-bond acceptor. If a three-dimensional grid point is proved to have neither the property of hydrogen-bond donor nor hydrogen-bond acceptor, the point is assumed to have no hydrogen-bonding property.

Hydrogen-bonding functional groups that are expected to form hydrogen bonds with the trial compound are selected from hydrogen-bonding functional groups present in the region of the biopolymer specified in the step S6 (S8). If a lot of hydrogen-bonding functional groups are present, they can be selected depending on the degree of importance. Furthermore, one or more dummy atoms are set to each hydrogen-bonding functional group selected in step S8 based on the three-dimensional grid point information calculated in S7 (S9).

In this step, a region in which a hydrogen-bond can be formed with each hydrogen-bonding functional group selected in step S8 (hydrogen-bonding region) is first determined based on the hydrogen-bonding grid point information calculated in step S7, and then a dummy atom is placed at the center of the hydrogen-bonding region comprising appropriate numbers of three-dimensional grid points, e.g., 5–20. The dummy atom is positioned within the hydrogen-bonding region and outside the van der Waals radii of other atoms. The hydrogen-bonding region is defined as a group of three-dimensional grid points that are neighboring to each other and have the same hydrogen-bonding properties. It should be noted that two or more dummy atoms may sometimes be placed from a single hydrogen-bonding functional group, or in contrast, no dummy atom may be generated. If the number of generated dummy atoms is large, it is preferred to reduce the number to 10 or less, more preferably 5 to 10, by selecting dummy atoms present in a bottom of the cavity of the ligand-bonding region considering the importance. To each dummy atom, the same hydrogen-bond property is assigned as that of the hydrogen-bonding region to which the dummy atom belongs.

Then, a trial compound is selected (S10) and then three-dimensional coordinates, hydrogen-bonding category numbers, information for molecular force-field calculation, and information for conformation generation are read from the "ADAM" format database prepared in S1 (S11). Then, correspondences are made combinatorially between the dummy atoms and the hydrogen-bonding heteroatoms in the trial compound (S12). If the number of dummy atoms is "m" and the number of hydrogen-bonding heteroatoms in the trial compound is "n", the number of the correspondences (combination) represented by N(i), in which number of hydrogen-bonds formed is "i", is mPi×nCi wherein symbol "P" represents permutations and symbol "C" represents combinations. It is preferred to generate all of the possible combinations of the dummy atoms and the hydrogen-binding heteroatoms in the trial compound.

Then, for all i's that satisfy the relationship $1_{min} \leq i \leq 1_{max}$, the steps S12–S39 are repeated. As a result, a total of $$\sum_{i=i_{min}}^{i_{max}} N(i)$$

sets of correspondences of dummy atoms and hydrogen-bonding heteroatoms in the trial compound are generated. By these procedures, all possible combinations of the hydrogen-bonds formed between the biopolymer and the trial compound are generated, and thereby all the binding modes between the trial compound and the biopolymer can be searched systematically and efficiently. It is preferred to set $1_{max}$ as the smaller number of the dummy atoms or the hydrogen-bonding heteroatoms, and set $1_{min}$ as the number smaller than $1_{max}$ by 2–4.

More specifically, one of the correspondences of the dummy atoms and the hydrogen-binding heteroatoms generated in S12 is selected (S13). In this step, correspondences in which the hydrogen-bonding properties of the dummy atoms do not match those of the hydrogen-bonding heteroatoms in the trial compound are not selected. Then, inter-atomic distances are calculated for all pairs of dummy atoms contained in the correspondence selected in S13 (S14). If both the number of dummy atoms and the number of hydrogen-bonding heteroatoms in the trial compound are 1, the process jumps to step S22 skipping steps S14–S21 and then jumps to step S26 skipping steps S23–S25. If either of the number of dummy atoms or the number of hydrogen-bonding heteroatoms in the trial compound is 1, the process jumps to step S22 skipping steps S14–S21.

The trial compound molecule is divided into a hydrogen-bonding part and a non-hydrogen-bonding part (S15), and rotatable bonds and their rotation modes in the hydrogen-bonding part divided in step S15 are selected (S16). Then, conformations of the trial compound are generated successively by rotating the bonds selected in step S16 according to the rotation modes inputted in the three-dimensional "ADAM" format database prepared in S1 (S17). For each generated conformation, subsequent steps S18–S29 are performed.

These steps will be detailed below. For each conformation generated in step S17, interatomic distances are calculated for all pairs of hydrogen-bonding heteroatoms in the trial compound contained in the correspondence selected in step S13 (S18). The interatomic distances of hydrogen-bonding heteroatoms are compared with those of corresponded dummy atoms. If the value of "F", which is a sum of the squares of the differences between the dummy-atom/dummy-atom distances as calculated in step S14 and the heteroatom/heteroatom distances of the trial compound as calculated in step 18, is outside a given range, the correspondence is excluded as inappropriate in the conformation (S19). That is, when F is calculated by the following equation:

$$F = \sum_{i=1}^{n(n-1)/2} (r_{li} - r_{di})^2$$

hydrogen-bonding correspondences and conformations of the trial compound which do not satisfy the following condition are excluded:

$k_a \leq F \leq k_a'$ wherein "n" is the number of hydrogen bonds; "$r_{di}$" is the i-th distance between dummy atoms; and "$r_{li}$" is the i-th distance between hydrogen-bonding heteroatoms in the trial compound; "$k_a$" is the lower limit of F; and "$k_a'$" is the upper limit of F. The value of $k_a$ is preferably 0.6–0.8 and that of $k_a'$ is preferably 1.2–1.4. In this step, possible hydrogen-bonding schemes between the biopolymer and the trial compounds and possible conformations of the ligand molecule can be searched efficiently and thoroughly.

Then, for the hydrogen-bonding correspondences and conformations not excluded in step S19, the conformation of the hydrogen-bonding part of the trial compound is optimized by minimizing the value of F (S20). With this step, the conformation of the trial compound is corrected so that the biopolymer and the trial compound can form stable hydrogen bonds. The conformation of the hydrogen-bonding part of the trial compound can be optimized by minimizing the value of F using the Fletcher-Powell method (Fletcher, R., Powell, M. J. D., Computer J., 6, 1968, p. 163), treating the torsion angles of the rotatable bonds present in the hydrogen-bonding part as variables.

Then, the intramolecular energy is calculated for the hydrogen-bonding part of the trial compound optimized in step S20, and the conformations with intramolecular energies higher than given threshold are excluded (S21). For example, when the intramolecular energy of the hydrogen-bonding part of the trial compound is calculated by using the molecular force field of AMBER 4.0, conformations with an intramolecular energy of more than 100 kcal/mol are preferably excluded. Then, the atomic coordinates of the trial compound is converted to the coordinate system of the biopolymer so that the coordinates of the hydrogen-bonding heteroatoms in the trial compound in the conformation obtained in step S21 coincide with those of the corresponded dummy atoms (S22). The Kabsh's method of least squares can be used for this step (Kabsh, W., Acta Cryst., A32, 1976, p. 922; Kabsh W., Acta Cryst., A34, 1978, p. 827). By these procedures, likely hydrogen-bonding schemes and the conformations of the hydrogen-bonding part of the trial compound can be estimated roughly at the same time.

Following the above step, the intermolecular interaction energy between the biopolymer and the hydrogen-bonding part of the trial compound (the sum of a van der Waals interaction energy and an electrostatic interaction energy) and the intramolecular energy of the hydrogen-bonding part of the trial compound are calculated (S23). The intermolecular interaction energy between the biopolymer and the hydrogen-bonding part of the trial compound $E_{inter}$ can be calculated by the following equation:

$$E_{inter} = \sum_{k} [G_{vdw}(k_0) + G_{elc}(k_0) \cdot q_k]$$

wherein "k" is a sequential number for the atoms in the trial compound; "$G_{vdw}(k_0)$" and "$G_{elc}(k_0)$" are the van der Waals and the electrostatic interaction energies of the grid point information at the grid point at ko closest to the atom "k"; "qk" is the atomic charge of the atom k.

The intramolecular energy of the hydrogen-bonding part of the trial compound $E_{intra}$, can be calculated by known methods. For example, $E_{intra}$ can be calculated by the following equation using a reported force field such as AMBER4.0:

$$E_{intra} = \sum_{dihedrals} \sum_{n} \frac{V_n}{2}[1 + \cos(n\Phi - \gamma)] + \sum_{i<j}(A_{ij}/R_{ij}^{12} - B_{ij}R_{ij}^6) + \sum_{i<j}(q_i q_j / \varepsilon R_{ij})$$

wherein "$V_n$" is a constant provided for force-field atom types of four atoms constituting a torsion angle; "n" is a constant representing the symmetry of the torsion-angle potential; $\Phi$ is a torsion angle, $\gamma$ is the phase of the torsion-angle potential (provided for force-field atom types of four atoms constituting a torsion angle); "$A_{ij}$" and "$B_{ij}$" are constants for a pair of force-field atom types of the i-th and j-th atoms in the trial compound; "$R_{ij}$" is the distance between the i-th and j-th atoms; $q_i$ is the atomic charge on the i-th atom in the trial compound; $q_j$ is the atomic charge on the j-th atom in the trial compound, and $\varepsilon$ is a dielectric constant.

Conformations of the trial compound are excluded if the sum of the intermolecular interaction energy and intramolecular energy as calculated in step S23 is higher than a given threshold (S24). For example, conformations in which the sum of these energies is higher than 10 kcal/mol per 100 dalton of molecular weight can be excluded. Then, the structure of the hydrogen-bonding part of the trial compound is optimized if it was not excluded in step S24 (S25). The structures of the hydrogen-bonding part of the trial compound can be optimized by optimizing the torsion angles of the hydrogen-bonding part of the trial compound as well as the relative location and orientation of the trial compound.

For example, the structure of the hydrogen-bonding part of the trial compound can be optimized by the Powell method (Press, W. H., Flannery, B. P., Teukolsky, S. A., Vitterling, W. T., "Numerical Recipes in C", Cambridge University Press, Cambridge, 1989) or the like, so that the total energy $E_{total}$ calculated by the following formula is minimized:

$$E_{total} = E_{inter} + E_{intra} + W_{hb} \cdot N_{hb} \cdot C_{hb}$$

wherein $E_{inter}$ and $E_{intra}$ are the same as those defined above; "$W_{hb}$" is a weight; "$N_{hb}$" is the number of hydrogen-bonds; and "$C_{hb}$" is a constant energy value assigned for one hydrogen-bond (e.g., 2.5 kcal/mol).

Then, conformations of the trial compounds are successively generated by rotating the rotatable bonds in the non-hydrogen-bonding part of the trial compound according to the rotation mode inputted in the "ADAM" format three-dimensional database prepared in S1 (S26), and steps S27–S30 are repeated for each generated conformation. Specifically, the intermolecular interaction energy between the biopolymer and the trial compound and the intramolecular energy of the trial compound are calculated (S27), and conformations of the trial compound are excluded if the sum of the intermolecular interaction energy and intramolecular energy as calculated in S27 is higher than a given threshold (S28). The entire structure of the trial compound having conformations not excluded in step S28 are then optimized (S29), and the energies are calculated for docking structures of the biopolymer and the trial compound obtained by S29, and the most stable docking structure with the minimum energy is selected (S30).

The intermolecular interaction energy and intramolecular energy can be calculated in the same manner as S23, provided that energies should be calculated for the whole structure of the trial compound in S27, whereas energies are calculated only for the hydrogen-bonding part of the trial compound in S23. As the upper limit for the sum of these energies, for example 10 kcal/mol per 100 dalton of molecular weight can be used. Through this step, stable docking structures comprising the biopolymer and the trial compound as well as active conformations of the trial compound can be obtained. The optimization of the structures of the trial compound can be carried out in the same manner as S25, provided that the optimization should be performed for the whole structure of the trial compound in S29, whereas the optimization is directed only to the hydrogen-bonding part of the trial compound in S25.

The docking process of the biopolymer and the trial compound as described above can be carried out by using the automated docking program "ADAM" (PCT International Publication WO93/20525; Yamada, M. and Itai, A., Chem. Pharm. Bull., 41, 1993, p. 1200; Yamada, M. and Itai, A., Chem. Pharm. Bull., 41, 1993, p. 1203; Yamada Mizutani, M., Tomioka, N., and Itai, A., J. Mol. Biol., 243, 1994, pp. 310–326).

Whether or not the trial compound should be selected as a ligand-candidate compound is decided based on all or part of the given criteria including the intermolecular interaction energy between the biopolymer and the trial compound, the intramolecular energy of the trial compound, number of hydrogen bonds, number of rings and others, which is evaluated in the most stable docking structure obtained in S30 (S31). Examples of the intermolecular interaction energy include electrostatic interaction energy, van der Waals interaction, hydrogen bond energy, and sum of them. For example, a trial compound with sum of the electrostatic and van der Waals interaction energies below –2 kcal/mol per molecular weight of 100 dalton can be selected as a ligand-candidate compound. Then, judgement is performed whether or not all of the trial compounds have been subjected to the selection (S32), and if not all of the trial compounds have been subjected to the selection, the steps of S10–S31 are repeated by returning to the step S10, and if the selection has been completed, the process proceeds to the step of S33.

More promising ligand-candidate compounds are further selected from the ligand-candidate compounds selected in S31 (S33). Prior to the further selection, it is convenient to decide another criteria for the further selection by referring to a list of information about the ligand-candidate compounds in their most stable docking structures, e.g., the intermolecular interaction energy between the biopolymer and the trial compound, the intramolecular energy of the trial compound, the number of hydrogen bonds, and the number of rings and others. For example, a further selection is preferably carried out using more severe criteria comprised of the number of hydrogen bonds that are formed between the biopolymer and the ligand-candidate compound, the intermolecular interaction energy between the biopolymer and the ligand-candidate compound, and the number of atoms.

Examples of the intermolecular interaction energy include electrostatic interaction energy, van der Waals interaction, and sum of them. For example, trial compounds with the sum of the electrostatic and van der Waals interaction energies below –8 kcal/mol per molecular weight of 100 dalton are preferably selected as ligand-candidate compounds. Although arbitrary number can be specified as a criterion of the number of hydrogen bonds depending on the sort of the biopolymer, it is desirable to apply a number of, for example, 2 or more, more preferably 3 or more as the criterion. Criterion about the number of atoms may also be arbitrary, but the number of, for example, 20 or more, preferably in the range of 20 to 40 can be specified as the criterion.

If too many dummy atoms are generated from the biopolymer, or if the trial compound has rather high conformational flexibility or has a lot of heteroatoms, according to a more preferred embodiment of the present invention, information about the trial compound is inputted according to the step S9, and then steps S13–S25 are carried out for a partial structure of the trial compound and preserve information about correspondences of dummy atoms and hydrogen-bonding heteroatoms of the trial compound that provide impossible hydrogen-bonding schemes and hydrogen-bonding heteroatoms that cannot be corresponded with any dummy atom in the partial structure. Although the partial structure of the trial compound can be arbitrarily specified without any structural restrictions, a partial structure containing at least three hydrogen-bonding functional groups is preferred. Presence or absence of conformational flexibility in the partial structure may be disregarded.

Subsequent to the above step, the steps of S13–S33 are performed for the whole structure of the trial compound, excluding, from the set of correspondences prepared in the step S12, the correspondences containing the hydrogen-bonding heteroatoms and the correspondences of dummy atoms and hydrogen-bonding heteroatoms preserved in the previous step. As a result, the number of the correspondences and conformations to be examined can be reduced, thereby time for structural searching for stable docking structure of the biopolymer and the trial compound can be greatly shortened (this method is sometimes referred to as the "Pre-Pruning method (PP method)"). The PP method is based on the assumption that any hydrogen-bonding schemes and ligand conformations that are impossible in the partial structure of the trial compound are also impossible in the whole structure of the trial compound. By applying the PP method, the time for the search can be remarkably shortened without affecting the accuracy and reliability of the resulted docking structure of the biopolymer and the trial compound.

EXAMPLE

In order to verify the effectiveness of the method of the present invention, calculations were carried out using a dihydrofolate reductase as the target biopolymer as to whether or not the substrates or known inhibitors, or analogues thereof can be selected as ligand-candidate compounds.

As the atomic coordinates of the dihydrofolate reductase (hereinafter referred to as "DHFR"), the values obtained from the atomic coordinates of the binary complex of *E. Coli* DHFR and methotrexate available from the Protein Data Back entry 4DFR were used. The atomic coordinates of a cofactor NADP$^+$ molecule were added to the atomic coordinates of the binary complex on the basis of the crystal structure of the ternary complex of DHFR, folic acid, and NADP$^+$. All water molecules were eliminated from the atomic coordinates of the binary complex, except for the two water molecules that strongly bind to DHFR and cannot be chemically removed. One of the two water molecules not eliminated binds to tryptophan 21 and aspartic acid 26 of DHFR through hydrogen-bonds, and the other binds to leucine 114 and threonine 116.

As a database of trial compounds, the Available Chemicals Directory (ACD-3D, MDL) containing about 110,000 molecule data was used. Among the compounds stored in the database, the following molecules were excluded: molecules with 5 or less atoms; molecules consist of only H, C, Si and halogen atoms; molecules containing atoms other than H, C, N, O, S, P and halogen atoms; molecules with 6 or more rotatable bonds; and molecules having no ring structure, and 10,017 compounds were subjected to the search. The data were supplemented with hydrogen atoms, and force-field atom-type numbers, hydrogen-bonding category numbers, atomic charge, and bond-rotation modes (rotation with a rotation angle of 120°) were assigned. The criteria for the selection of ligand-candidate compounds were as follows: the intermolecular interaction energy between the target biopolymer (the enzyme) of −7 kcal/mol or less per molecular weight of 100 dalton, 3 or more intermolecular hydrogen bonds, and 25 or more number of atoms.

Figure 3:
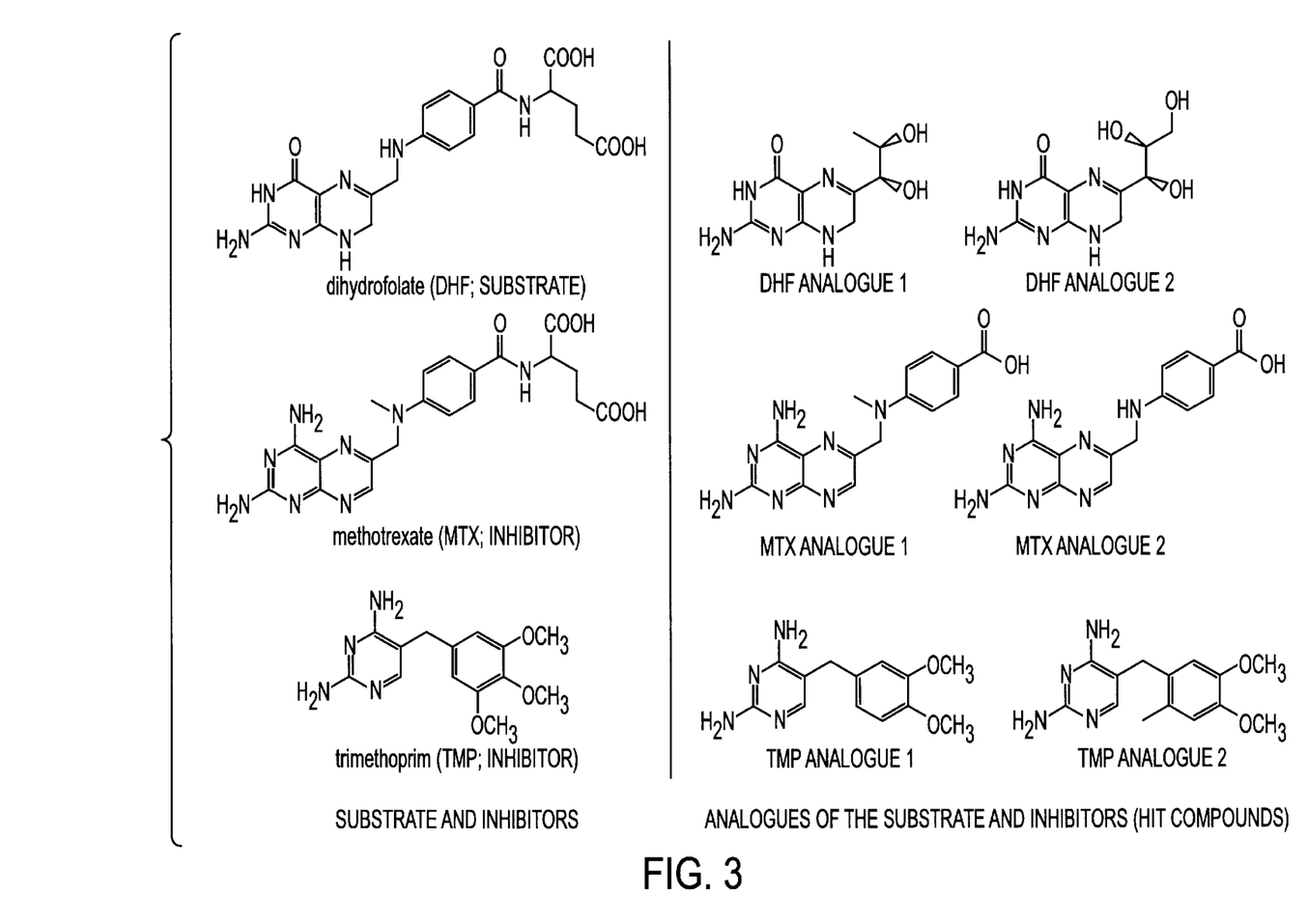
FIG. 3 shows examples of the substrate and known inhibitor analogues for a dihydrofolate reductase selected as ligand candidate compounds by the method of the present invention.

According to the method of the present invention, about 1400 trial compounds were finally selected as ligand-candidate compounds, and the process required about 80 hours from inputting of three-dimensional coordinates of the biopolymer until the completion of the selection of the ligand-candidate compounds. These ligand-candidate compounds included the compounds shown in FIG. 3, together with other numerous analogues to substrates and known inhibitors. An inhibitor, methotrexate, and the substrate, dihydrofolate, were not selected from this search because of the limitation about the number of rotatable bonds, while trimethoprim was selected as a ligand candidate compound. The binding modes and the conformations of the ligand candidate compounds selected by the method of the present invention agreed well with the binding modes and the conformations deduced from the crystal structures of the complexes comprising the substrate or the inhibitor analogue together with the enzyme.

Figure 4:
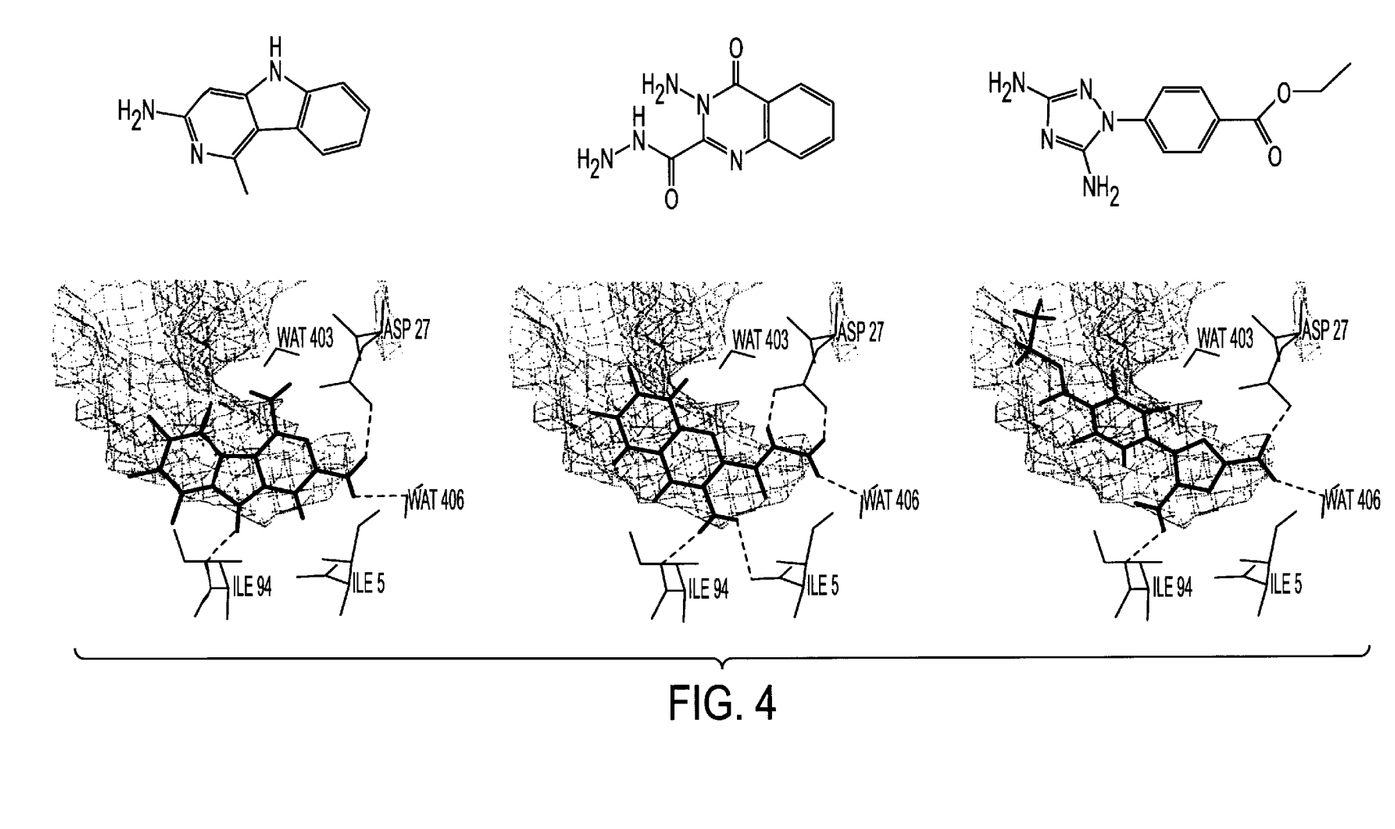
FIG. 4 shows examples of ligand-candidate compounds with novel structures for a dihydrofolate reductase obtained by the method of the present invention.

According to the method of the present invention, numerous ligand-candidate compounds with novel structures quite dissimilar to the substrate and the known inhibitors were selected. A part of examples thereof are shown in FIG. 4 together with the estimated docking structures. In the figure, the bold line indicates the molecular skeletons of the selected ligand-candidates, the dotted line indicates hydrogen bonds, the fine solid line indicates a part of the biopolymer, and the cage depicted with the broken line indicates regions allowed for the centers of the atoms of the ligand. From these docking structures, it was found that that several hydrogen bonds were formed and high complementarities with the enzyme cavity were achieved by selected ligand-candidates. Therefore, these ligand candidate compounds are promising lead compounds as inhibitors against dihydrofolate reductase.

Industrial Applicability

According to the method of the present invention, ligand compounds to the target biopolymer whose structure is already known, can be identified from a three-dimensional structure database in a short time, while considering conformational flexibility, thereby extremely reliable searching results can be easily obtained. The method of the present invention is thus useful in the field of medical and biological sciences for the creation of lead compounds having activities as inhibitors, agonists, or antagonist to biopolymers.

What is claimed is:

1. A method of searching one or more ligand compound to a target biopolymer from a three-dimensional structure database, which comprises the steps of:
   (i) the first step of assigning hydrogen-bonding category numbers, information for calculating force-field energy, and information for generating conformations, to two or more trial compounds, in addition to atomic three-dimensional coordinates thereof;
   (ii) the second step of preparing physicochemical information about a ligand-binding region and one or more dummy atoms based on the three-dimensional atomic coordinates of the target biopolymer;
   (iii) the third step of estimating the most stable docking structure through structural optimization, wherein said step further comprises the steps of generating possible docking structures by docking a trial compound to the biopolymer while varying conformations of the trial compound, and evaluating interaction energy between the target biopolymer and the trial compound, based on the hydrogen-bonding category number, the information for calculating force-field energy, and the information for generating conformations assigned to the trial compound in addition to the three-dimensional coordinates according to the step (i) and based on the physicochemical information about the ligand-binding region prepared in the step (ii);
   (iv) the fourth step of deciding whether or not the trial compound should be adopted as a ligand candidate compound based on given criteria including the interaction energy values between the target biopolymer and the trial compound in the most stable docking structure found according to the step (iii); and
   (v) the fifth step of repeating the step (iii) and the step (iv) for all of the trial compounds.

2. The method according to claim 1, wherein the third step further comprises the steps of:
   (1) step (a) of searching likely binding modes between the biopolymer and the trial compound by preparing all of the combinatorial correspondences between hydrogen-bonding heteroatoms in the trial compound and dummy atoms placed at the positions of heteroatoms that can be hydrogen-bonding partners of hydrogen-bonding functional groups in the biopolymer;
   (2) step (b) of simultaneously estimating possible hydrogen-bonding schemes between the biopolymer and the trial compound and conformations of hydrogen-bonding part of the trial compound by comparing the distances between dummy atoms with the distances between the corresponded hydrogen-bonding heteroatoms while systematically changing the conformations of the trial compound; and
   (3) step (c) of obtaining the structure of a docking structure comprising the biopolymer and the trial compound by converting the atomic coordinates of the trial compound to the coordinate system of the biopolymer for each hydrogen-bonding scheme and conformation obtained in the step (b) based on the correspondences between the hydrogen-bonding heteroatoms in the trial compound and the dummy atoms.

3. The method according to claim 1, wherein the third step further comprises the steps of:

(1) step (a) of searching likely binding modes between the biopolymer and the trial compound by preparing all of the combinatorial correspondences between hydrogen-bonding heteroatoms in a partial structure of the trial compound and the dummy atoms placed at the positions of heteroatoms that can be hydrogen-bonding partners of hydrogen-bonding functional groups in the biopolymer;

(2) step (b) of simultaneously estimating hydrogen-bonding schemes between the biopolymer and the trial compound and conformations of the partial structure of the trial compound by comparing the distances between dummy atoms with the distances between the corresponded hydrogen-bonding heteroatoms while systematically changing the conformations of the trial compound;

(3) step (c) of preserving correspondences of the dummy atoms and the hydrogen-bonding heteroatoms that provide impossible hydrogen-bonding schemes in the partial structure of the trial compound, and hydrogen-bonding heteroatoms that cannot form any hydrogen-bond with the dummy atoms based on the hydrogen-bonding schemes and conformations obtained in the step (b);

(4) step (d) of searching likely binding modes between the biopolymer and the trial compound by preparing all of the combinatorial correspondences between dummy atoms and hydrogen-bonding heteroatoms in a the whole structure of the trial compound, excluding the correspondences containing the hydrogen-bonding heteroatoms preserved in the step (c) and the correspondences containing the dummy atoms and hydrogen-bonding heteroatoms preserved in the step (c);

(5) step (e) of simultaneously estimating possible hydrogen-bonding schemes between the biopolymer and the trial compound and conformations of hydrogen-bonding part of the trial compound by comparing the distances between dummy atoms with the distances between corresponded hydrogen-bonding heteroatoms while systematically changing the conformations of the trial compound; and (6) step (f) of obtaining the structure of a docking structure comprising the biopolymer and the trial compound by converting the atomic coordinates of the trial compound to the coordinate system of the biopolymer for each hydrogen-bonding scheme and conformations obtained in the step (e) based on the correspondences between the hydrogen-bonding heteroatoms in the trial compound and the dummy atoms.

4. The method according to claim 1, wherein the third step further comprises the steps of:

(1) step (a) of searching likely binding modes between the biopolymer and the trial compound by preparing all of the combinatorial correspondences between hydrogen-bonding heteroatoms in the trial compound and dummy atoms placed at the positions of heteroatoms that can be hydrogen-bonding partners of hydrogen-bonding functional groups in the biopolymer;

(2) step (b) of simultaneously estimating possible hydrogen-bonding schemes between the biopolymer and the trial compound and conformations of hydrogen-bonding part of the trial compound by comparing the distances between dummy atoms with the distances between hydrogen-bonding heteroatoms while systematically changing the conformations of the trial compound;

(3) step (c) of optimizing the conformations of the trial compound so that the positions of the dummy atoms and the hydrogen-bonding heteroatoms in the trial compound can be in accord with each other while retaining the hydrogen-bonding scheme obtained in the step (b), and then excluding the conformations of the trial compound having high intramolecular energies;

(4) step (d) of obtaining the structure of a complex comprising the biopolymer and the trial compound by converting the entire atomic coordinates of the trial compound to the coordinate system of the biopolymer for each conformation not excluded in the step (c) based on the corresponding relationships between the hydrogen-bonding heteroatoms in the trial compound and the dummy atoms;

(5) step (e) of excluding from docking structures of hydrogen-bonding parts obtained in the step (d) the docking structures in which intramolecular energies of the hydrogen-bonding parts of the trial compound and intermolecular energies between the biopolymer and the hydrogen-bonding parts of the trial compound are high, and then carrying out structure optimizations of the remaining docking structures;

(6) step (f) of obtaining new docking structures comprising the whole trial compound by generating the conformations of non-hydrogen-bonding parts of the trial compound for each docking structure obtained in the step (e); and (7) step (g) of excluding from the docking structures obtained in the step (f) the docking structures in which intramolecular energies of the whole structure of the trial compound and intermolecular energies between the biopolymer and the trial compound are high, and then carrying out structure optimizations of the remaining docking structures.

5. A ligand compound for a biopolymer which is retrieved by a method according to claim 1.

* * * * *